United States Patent
Schweighofer

(10) Patent No.: US 9,894,899 B1
(45) Date of Patent: Feb. 20, 2018

(54) COMPOSITION TO TREAT CITRUS GREENING DISEASE AND A METHOD OF APPLYING THE COMPOSITION

(71) Applicant: Edward Schweighofer, Tyler Hill, PA (US)

(72) Inventor: Edward Schweighofer, Tyler Hill, PA (US)

( * ) Notice: Subject to any disclaimer, the term of this patent is extended or adjusted under 35 U.S.C. 154(b) by 0 days.

(21) Appl. No.: 14/663,186

(22) Filed: Mar. 19, 2015

(51) Int. Cl.
*A01N 25/30* (2006.01)
*A01N 37/46* (2006.01)
*A01N 59/16* (2006.01)

(52) U.S. Cl.
CPC .............. *A01N 25/30* (2013.01); *A01N 37/46* (2013.01); *A01N 59/16* (2013.01)

(58) Field of Classification Search
None
See application file for complete search history.

(56) References Cited

U.S. PATENT DOCUMENTS

2007/0148200 A1* 6/2007 Stringfellow .......... A01N 25/30 424/405
2007/0166340 A1* 7/2007 Stringfellow .......... A01N 25/00 424/405

OTHER PUBLICATIONS

Stansly et al., "Vector control and foliar nutrition to maintain economic sustainability of bearing citrus in Florida groves affected by huanglongbing", Pest Manag Sci 70: 415-426 (2014).*
Tecmangam MSDS [downloaded from the website https://www.harrells.com/resources/exports/file?n=200037&t=sds on Mar. 31, 2016].*
KPhite 7LP AG-Booklet [downloaded from the website http://www.plantfoodsystems.com/wp-content/uploads/2015/08/K-PHITE-7LP-AG-Booklet.pdf on Mar. 31, 2016].*
Sidnam, "Gardening: How to care for mature citrus trees", LA Times (1993).*
Antibiotic entry—Biology Dictionary 2016.*
Exhibit A.*
Exhibit B.*
Exhibit C.*
Exhibit D.*
Exhibit E.*
Exhibit F.*
Exhibit G.*
Exhibit H.*
Exhibit I.*
Exhibit J.*
Exhibit K.*
Exhibit L.*
Exhibit M.*
Exhibit N.*
Exhibit O.*
Van Vuuren et al., "Preliminary report on extended treatment of citrus greening with tetracycline hydrochloride by trunk injection", Plant Dis Reptr 61: 358-359 (1977).*
James Graham, University of Florida. Citrus Advanced Technology Program Quarterly & Final Reports: Control of Citrus Greening, Canker & Emerging Diseases of Citrus. Jul. 21, 2014.

* cited by examiner

*Primary Examiner* — Robert A Wax
*Assistant Examiner* — Thor Nielsen
(74) *Attorney, Agent, or Firm* — Gable Gotwals

(57) ABSTRACT

A composition for treating a citrus tree having citrus greening disease includes an antibiotic, at least one micronutrient, water, and a bark penetrating surfactant like organosiloxane surfactant that is absorbed through the bark periderm and enters the lenticels of the tree. The antibiotic is one effective for treating a gram negative bacteria like HLB and is preferably tetracycline. The micronutrient can be zinc, manganese, or iron (and is preferably all three), and the zinc and manganese can be in sulfate form to serve as a bactericide. A pH adjusting compound such as ammonium sulfate can be included to adjust the pH of the water. A method of treating citrus greening disease using the composition includes the step of applying the composition onto the bark periderm of a citrus tree. The applying step results in the composition entering the vascular system of the citrus tree.

8 Claims, No Drawings

COMPOSITION TO TREAT CITRUS GREENING DISEASE AND A METHOD OF APPLYING THE COMPOSITION

BACKGROUND OF THE INVENTION

This invention relates to systems, compositions, and methods directed toward treating Huanglongbing, also known as HLB or citrus greening disease. More specifically, the invention relates to compositions that address the bacteria causing the disease and do not require the use of pesticides nor mechanical penetration of the bark periderm.

Citrus greening disease is a bacterial plant disease that is spread from one citrus tree to the next by a small insect called the Asian citrus pysllid. The bacteria, phloem-limited *Liberibacter asiaticus*, is a gram negative bacteria that travels throughout the tree's system and begins to destroy the fine roots of the tree (and therefore the tree's vascular system), making the tree unable to maintain its tree canopy. As the disease progresses, the tree's leaves begin to yellow on one side more than the other and become as small as mouse or rat ears, the tree produces small and lopsided fruit, and the fruit prematurely drops from the tree. If left untreated, the tree eventually dies.

To date, there is no cure or effective treatment for citrus greening disease. Most treatments involve a combination of spraying an insecticide like carbaryl, imidacloprid and aldicarb to kill the Asian citrus pyslli and micronutrients such as manganese and boron directly on the leaves. Potassium salicylate can also be applied. However, academic studies have not shown that enhanced foliar nutrition does anything to counteract the disease. As soon as the treatment is stopped, the symptoms return. Additionally, the insecticides can find their way into consumer products like orange juice and pose a risk to consumer health.

Other treatments require injecting an antibiotic like tetracycline and penicillin into the trees. Sometimes the tetracycline is used alone or followed by the penicillin. Other times the tetracycline is combined with soluble copper or zinc sulfate. Regardless, the treatment usually occurs two or more times at regular intervals and comprises trunk integrity. Injection requires drilling a hole into the tree about half the depth of the tree's trunk diameter, installing an injection screw into the hole, and coupling a supply hose to the screw. After treatment the hole is sealed. Drilling might be a good way to get antibiotics and insecticides into the phloem and xylem of a tree. However, it is labor-intensive, weakens the trunk, and leaves the trunk vulnerable for another bacteria, fungus, or insect to enter the trunk at a later time.

Some other treatments involve injecting the trunk or drenching the soil of non-bearing trees with chelated copper formulations such as MAGNA-BON® Agri-San soluble copper sulfate pentahydrate (Magna-Bon II LLC) and COP-R-QUIK® soluble copper (Natural Ag Solutions, LLC). Treatments must be done at three-month intervals over more than one growing season. Copper is a very good bacteriacide for a lot of different ailments in a wide range of plants, so is zinc, manganese and any nutrient that has sulfate in it. However, in most orange groves the copper levels in the soil test are extremely high because of the copper's continual use.

Other solutions take a genetic route and seek to provide a more sustainable root stock or strain that is immune to the gram-negative bacteria. In the meantime, until the gram bacteria is killed and the roots restored, the symptoms keep reoccurring. including loss of fine feeder roots which leads to tree canopy loss and small, oblong fruit that falls prematurely off the tree.

SUMMARY OF THE INVENTION

A composition for treating a citrus tree having citrus greening disease includes an antibiotic, at least one micronutrient, water, and a bark penetrating surfactant that is absorbed through the bark periderm and carries the antibiotic and micronutrient into the lenticels of the tree. The bark penetrating surfactant is preferably an organosiloxane surfactant. The antibiotic is one effective for treating a gram negative bacteria and is preferably tetracycline. The micronutrient can be zinc, manganese, or iron—preferably all three—and the zinc and manganese can be in sulfate form to serve as a bactericide. A pH adjusting compound such as ammonium sulfate can be included to adjust the pH of the water.

The preferred formula for the composition per acre of treatment is:
- 1.5 pounds of tetracycline;
- 1.5 gallons of organosiloxane surfactant;
- 10 lbs. of spray grade zinc sulfate;
- 10 lbs. of spray grade manganese sulfate;
- 1 gallon of chelated iron; and
- 10 lbs. of ammonium sulfate.

The composition is then added to 100 gallons of water.

A method of treating citrus greening disease using the composition includes the step of applying the composition onto the bark periderm of a citrus tree. The applying step results in the composition entering the vascular system of the citrus tree. All necessary micronutrients to enhance tree health can be applied in addition to the composition.

Objectives of this invention include providing a composition and method of application that (1) treats the bacterial infection causing citrus greening disease; (2) takes advantage of a tree's vascular system; (3) does not require mechanical penetration of the bark periderm or soaking of the soil surrounding the tree; (4) avoids the use of pesticides or different or additional quantities of pesticides beyond those typically used; (5) can make use of conventional agricultural equipment such as an air blast or speed sprayer or its equivalent; (6) can be done in a single treatment and does not require multiple treatments of a tree during the growing season; (7) does not require the use of soluble copper alone or in combination with an antibiotic; and (8) can be applied during or prior to the tree bearing fruit.

DETAILED DESCRIPTION OF THE PREFERRED EMBODIMENTS

A composition for treating citrus greening disease, and for treating other gram-negative bacteria-caused problems like citrus canker, includes a bark penetrating surfactant to deliver an antibiotic and micronutrients to the tree's vascular system. The composition does not make use of pesticides or soluble copper, does not require any mechanical penetration of the bark or soaking of the soil surrounding the tree, and can be applied to the bark periderm with a standard air blast sprayer such as a speed sprayer.

In a preferred embodiment, the bark penetrating surfactant is an organosiloxane surfactant or its equivalent. PEN-TRA-BARK® bark penetrating surfactant (Quest Products Corp.)—a composition of alkylphenol ethoxylate, polysiloxane polyether copolymer, and propylene glycol—is a suitable organosiloxane surfactant.

The composition also preferably includes a pH lowering component such as ammonium sulfate or its equivalent to lower the pH level of the water so the surfactant, antibiotic and micronutrients can more easily enter the tree's bark and leaves. Plants absorb nutrients and herbicides better when the pH level is acidic. Preferably, the pH of the water is adjusted to be in a range of 5.5 to 6.5 (slightly acidic).

The antibiotic is preferably a tetracycline antibiotic or its equivalent. MYCOSHIELD® bactericide (NuFarm Americas, Inc.), an oxytetracycline calcium complex, is a suitable antibiotic. The tetracycline does not need to be combined with soluble copper, nor is another antibiotic such as penicillin required to follow its application.

The micronutrients include zinc, manganese, and iron, with the zinc and manganese components preferably being in sulfate form to serve as a bactericide.

The preferred formula for the composition per acre of treatment, assuming 100 gallons of water per acre, is:
  1.5 pounds of tetracycline
  1.5 gallons of organosiloxane surfactant;
  10 lbs. of spray grade zinc sulfate;
10 lbs. of spray grade manganese sulfate;
1 gallon of chelated iron; and
10 lbs. of ammonium sulfate.

In addition to treating citrus greening, a wide range of other micronutrients could be added to the formula to alleviate any other deficiencies that citrus trees might have. Those deficiencies can be detected through leaf samples or soil testing surveys.

If a user has already sprayed a mixture of some of the micronutrients that the citrus tree needs, the user would not repeat the spray with those same micronutrients. The main two ingredients are tetracycline and organosiloxane surfactant to combat citrus greening, along with at least two pounds of zinc and manganese sulfate (0.02 pounds per gallon of water) and at least one quart of chelated iron per 100 gallons of water (0.0025 gallons per gallons of water).

Organosiloxane surfactant like PENTRA-BARK® bark penetrating surfactant has a wide range of use on its label, as does tetracycline. For example, PENTRA-BARK® can be applied in amounts ranging from 1.5 to 2.5 gallons per 100 gallons of water (0.015 to 0.025 gallons per gallon of water) and the tetracycline can be applied in amounts as low as 0.5 pounds per 100 gallons of water (0.005 to 0.015 pounds per gallon of water). The effective amount depends on the severity of the tree's or grove's symptoms or condition at the time of application.

A method of applying the composition to a citrus tree or grove includes mixing the composition in water and using a speed sprayer or its equivalent to administer the composition. Preferably, 100 gallons of water is used per acre. The relative amounts can be scaled up or down, depending on the area to be sprayed. For example, the amounts could be scaled down so that a homeowner, with a single citrus tree, can apply the composition using a quart or gallon sprayer. Regardless of the size of the application, no mechanical penetration of the bark periderm is required to administer the application.

Because tetracycline has a 60-day hold time when used on peaches, nectarines, apples, and nut trees, and because citrus products like oranges do not have a label for tetracycline, it is preferred that the oranges are picked before treating the tree. However, subsequent testing has shown 60 days after treatment with tetracycline, the tetracycline does not appear in the oranges. As a result of that testing, it is expected that at least one state, Florida, will approve its use on citrus trees beginning in late 2015.

In tests and experiments conducted by the inventor, about 80 acres of early and mid-season orange trees infected with citrus greening disease were sprayed with the composition using the above method. Late-season (Valencia) orange trees were left untreated. As reported below, the treated trees showed an unmistakable difference in growth, color, leaf size, and overall health between the treated trees and the untreated trees.

Daily inspections revealed that the treated trees began to drop, on average, about 20 to 25 leaves on the first day following treatment, with the number of dropped leaves increasing daily. Younger, stronger, more robust trees did not lose as many leaves as older, weaker, less robust trees did. By day 10, every tree had a loss of about 15% of its leaf canopy. This loss indicated that the spray material had entered the vascular system of the tree.

After 10 days, the trees stopped dropping leaves. After two weeks, a small amount of color change occurred, with the leaves becoming a darker green, most likely due from the iron. At one month, new growth was appearing on the trees. The growth was the typical light green color of new flush and there appeared to be more new flush than in a typical, past (pre-disease) Spring even though it was the middle of March.

During this time, when it would rain one to two inches, the trees would color up with a nice green color. Then, as the ground dried out and more than 5 days passed without rain, the trees would begin to revert back to the paler green color.

At 45 days, more growth appeared and the blossoms were well underway. The new growth had a uniform color without the yellow tissue surrounding the green veins, indicating that the manganese and zinc were being absorbed); an overall darker green color, indicating that iron was being absorbed; and larger size leaves (2×4 inches to 4×6 inches), indicating that the bacteria which causes greening disease was being affected. However, if there was not enough rain, the color would dampen.

At 60 days, the color did not fade in the absence of rain and the growth of the tree canopy was greatly improving. The new growth on some of the younger trees measured out at 3 feet. The next row of trees could no longer be seen through an adjacent tree's canopy, whereas previously three or four rows could be seen through the canopy.

More importantly, digging underneath the trees revealed healthy white roots growing. This strongly indicated that the tetracycline had killed most if not all the HLB bacteria in the root system (which harbors most of the bacteria).

At 75 days the trees continued to improve. Standing at the end of a row and looking down the row, there was an unmistakable difference in growth, color, leaf size, and overall health between the treated trees and the Valencia trees which had been left untreated.

Table 1 below shows the box counts over three growing seasons for the same 80 acres and trees as described above, with the trees in the last season being treated with the composition as described above. Absent the treatment, and given the deteriorating condition of the trees, the box count would have decreased from the prior season's count of 11,815 boxes. However, the treated trees show signs of recovery, with new wood growth which blossomed and set with new crop by early summer. In the upcoming growing season, the trees, unexpectedly, have come out of dormancy earlier than healthy trees in surrounding, untreated groves and could be treated about 30 days sooner.

TABLE 1

Box counts of oranges produced per season.

| Type | Prior to HLB | Infected with HLB | Treated for HLB |
|---|---|---|---|
| Seasonal | 17,222 | 11,815 | 12,025 |
| Delayed | — | — | 640 |
| Total | 17,222 | 11,815 | 12,665 |
| % change | | −31 | +7 |

While preferred embodiments of the composition and method have been described, the invention itself is defined by the scope of the following claims and their requirements, including each requirement's full range of equivalents.

What is claimed:

1. A Huanglongbing treatment spray composition comprising:

water;

a tetracycline antibiotic in an amount being at least 0.005 pounds per gallon of water;

three micronutrients, one of the three micronutrients including zinc; another of the three micronutrients including manganese, and another of the three micronutrients including iron;

a bark penetrating surfactant in an amount being at least 0.015 gallons per gallon of water; and a pH adjusting compound in an amount effective to adjust a pH of the Huanglongbing treatment spray composition in a range of 5.5 to 6.5.

2. A Huanglongbing treatment spray composition according to claim 1 wherein the Huanglongbing treatment spray is soluble copper free.

3. A Huanglongbing treatment spray composition according to claim 1 further comprising the bark penetrating surfactant being an organosiloxane surfactant.

4. A Huanglongbing treatment spray composition according to claim 1 wherein an amount of at least one of the three micronutrients is at least 0.02 pounds per gallon of water.

5. A Huanglongbing treatment spray composition according to claim 1 wherein an amount of at least one of the three micronutrients is at least 0.0025 gallons per gallon of water.

6. A Huanglongbing treatment spray composition according to claim 1 further comprising at least one of the three micronutrients being in sulfate form.

7. A Huanglongbing treatment spray composition according to claim 1 wherein the pH adjusting compound is ammonium sulfate.

8. A Huanglongbing treatment spray composition comprising:

a tetracycline antibiotic in an amount being at least 0.005 pounds per gallon of water;

a micronutrient including zinc;

another micronutrient including manganese;

another micronutrient including iron;

a bark penetrating surfactant in an amount being at least 0.015 gallons per gallon of water; and a pH adjusting compound in an amount effective to adjust a pH of the Huanglongbing treatment spray composition in a range of 5.5 to 6.5.

* * * * *